United States Patent
Dean et al.

(10) Patent No.: US 6,710,878 B1
(45) Date of Patent: Mar. 23, 2004

(54) IN-LINE PARTICULATE DETECTOR

(75) Inventors: Anthony John Dean, Scotia, NY (US); Andrew Philip Shapiro, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/333,181

(22) Filed: Jun. 14, 1999

(51) Int. Cl.[7] .......................... G01N 21/09; G01N 21/49
(52) U.S. Cl. ..................... 356/436; 356/338; 356/441
(58) Field of Search .............................. 356/337, 338, 356/437, 436, 441; 250/339.13, 343

(56) References Cited

U.S. PATENT DOCUMENTS

| | | | |
|---|---|---|---|
| 3,358,148 A | * 12/1967 | Conklin et al. | 356/343 |
| 4,066,364 A | 1/1978 | Emerson | 356/207 |
| 4,270,049 A | * 5/1981 | Tanaka et al. | 250/227 |
| 4,713,964 A | 12/1987 | Ioannides | 73/116 |
| 4,784,486 A | 11/1988 | Van Wagenen et al. | 356/301 |
| 5,386,111 A | 1/1995 | Zimmerman | 250/227.25 |
| 5,470,154 A | 11/1995 | Nishizawa et al. | 374/141 |
| 5,482,371 A | 1/1996 | Nishizawa et al. | 374/20 |
| 5,506,673 A | 4/1996 | Kosaka et al. | 356/72 |
| 5,568,121 A | * 10/1996 | Lamensdorf | 340/539 |
| 5,615,954 A | 4/1997 | Nishizawa et al. | 374/17 |
| 5,742,064 A | 4/1998 | Infante | 250/458.1 |
| 5,751,423 A | 5/1998 | Traina et al. | 356/338 |

* cited by examiner

*Primary Examiner*—Zandra V. Smith
(74) *Attorney, Agent, or Firm*—Patrick K. Patnode; Christian G. Cabou

(57) ABSTRACT

An in-line particulate detector comprises a housing having an inner flow portion. The housing Is disposed between adjacent portions of pipeline to permit a fuel flow from a fuel source through the inner flow portion to a fuel consumer. A light source is positioned within the housing for emitting a light beam within the inner flow portion. A first photodetector is positioned within the housing to detect the full strength of the light beam. A second photodetector is positioned within the housing to detect low, baseline levels of the light beam. Circuitry is coupled to first and second photodetectors to monitor the ratio of light intensities. When a fuel containing particulates is introduced, the light beam is scattered and the intensity measured by the second photodetector will increase and the intensity measured by the first photodetector will decrease.

27 Claims, 3 Drawing Sheets

IN-LINE PARTICULATE DETECTOR

BACKGROUND OF THE INVENTION

This invention relates generally to particulate detectors and more specifically to in-line particulate and liquid droplet detectors for natural gas lines.

Industrial power generation gas turbine engines include a compressor for compressing air that is mixed with fuel and ignited in a combustor for generating combustion gases. The combustion gases flow to a turbine that extracts energy for driving a shaft to power the compressor and produces output power for powering an electrical generator, for example. The turbine is typically operated for extended periods of time at a relatively high base load for powering the generator to produce electrical power to a utility grid, for example. Exhaust emissions from the combustion gases are therefore a concern and are subjected to mandated limits.

Low emission combustion systems are designed to produce low emissions and high combustion efficiency while burning natural gas fuel that is assumed to be free of liquid or solid contaminants. In fact, pipeline gas is at times contaminated with condensed liquid hydrocarbons (to varying degrees) as well as other solid particulate contaminants. It is highly desirable to minimize the effects of these contaminants on gas turbine combustor performance, either by their removal or by robust combustor design. As low emission systems have become more prevalent in the field and exposed to a variety of natural gas sources while performing with lower and lower emission goals, the presence of varying amounts of liquid hydrocarbons in the fuel source has become an increasingly important operational issue.

The quality of natural gas supplied to gas turbines is an important variable in turbine performance. The principle component of natural gas is methane, which typically accounts for over 90% of the mass. Other components in natural gas may include heavier hydrocarbons, oils and water. In gas turbines equipped with combustors that premix fuel and air prior to ignition, the chemical composition of the gas is particularly important because of the potential for ignition to occur within the mixing zone. The effect of heavier hydrocarbons and oils in the gas stream is to lower the autoignition temperature of the mixture. Natural gas with high concentrations of these species is more likely to ignite in the mixing zone of the combustors than in an intended flame holder region.

Several approaches have been utilized to detect particulates or droplets in a gas pipeline including, for example, light scattering, acoustics, eddy currents, and capacitance methods. Most current approaches, however, require a slipstream of a total flow for samples and therefore may not be representative of the entire flow. Additionally, most current instruments are rather delicate, expensive and are typically not robust enough for long-term application in a gas pipeline and cannot be placed directly into a pipeline.

Accordingly, there is a need in the art for an improved particulate detector.

SUMMARY OF THE INVENTION

An in-line particulate detector comprises a housing having an inner flow portion. The housing is disposed between adjacent portions of pipeline to permit a fuel flow from a fuel source through the inner flow portion to a fuel consumer. A light source is positioned within the housing for emitting a light beam within the inner flow portion. A first photodetector is positioned within the housing to detect the full strength of the light beam. A second photodetector is positioned within the housing to detect low, baseline levels of the light beam. Circuitry is coupled to first and second photodetectors to monitor the ratio of light intensities. When a fuel containing particulates is introduced, the light beam is scattered and the intensity measured by the second photodetector increases and the intensity measured by the first photodetector decreases.

DETAILED DESCRIPTION OF THE INVENTION

Figure 1:
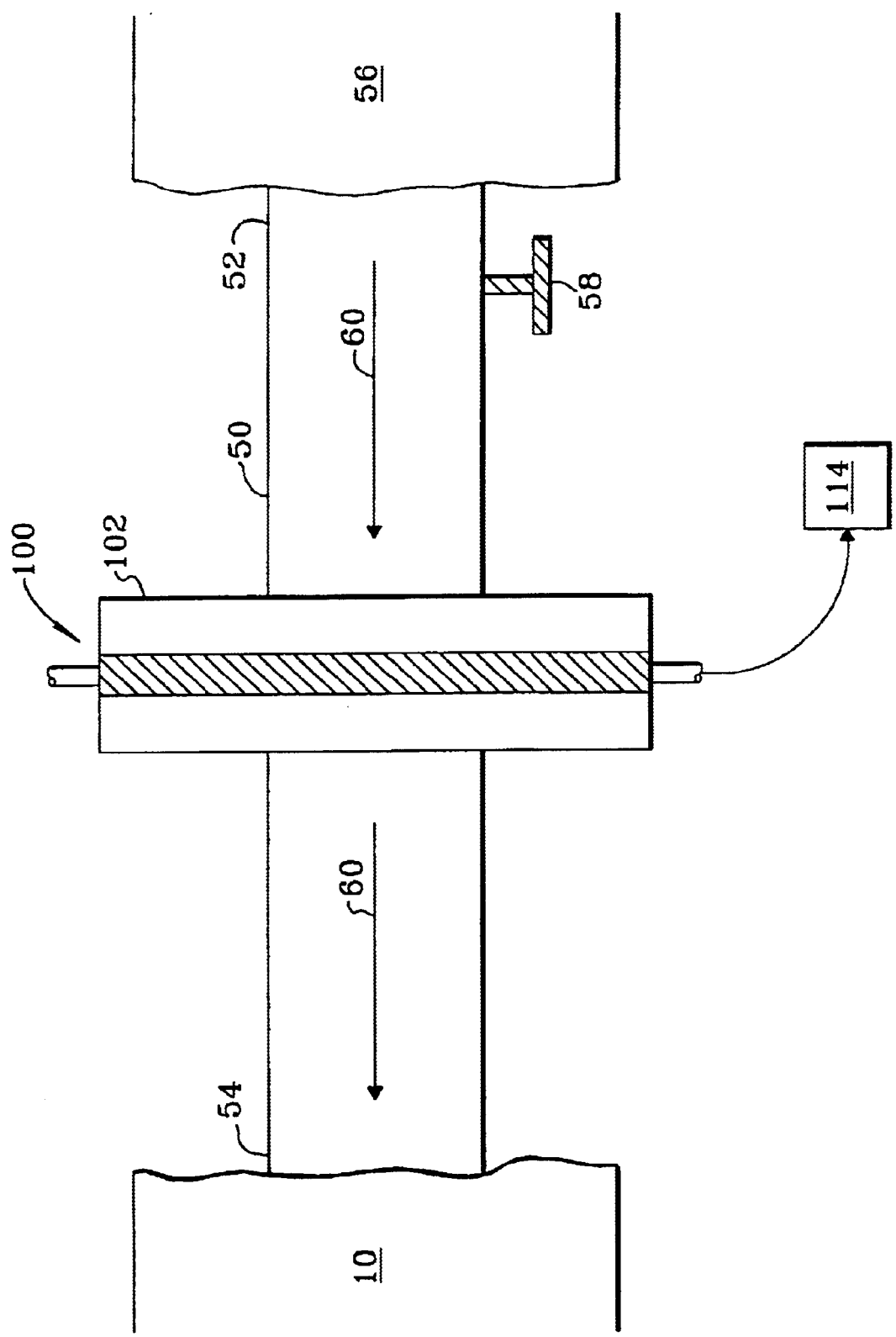
FIG. 1 is a schematic, cross-sectional side elevation view of a pipeline and an in-line particulate detector in accordance with one embodiment of the instant invention.

A pipeline 50 comprising an inlet 52 and an outlet 54 provides fluid communication between a fuel source 56 and a fuel consumer 10, for example a power turbine as shown in FIG. 1. A shut off valve 58 is typically disposed within pipeline 50, which valve 58 is movable between a fully open position and a fully closed position to allow or prevent fuel flow, respectively, from fuel source 56 to fuel consumer 10.

As discussed above, detecting that a proper fuel quality is present, prior to combustion within fuel consumer 10 is becoming increasingly important.

In accordance with one embodiment of the instant invention, an in-line particulate detector assembly 100 is coupled to pipeline 50. Typically, although not necessarily, in-line particulate detector assembly 100 is embodied within a housing 102, for example a flange, that is disposed between adjacent portions of pipeline 50 to permit a continuous fuel flow 60 from fuel source 56 to fuel consumer 10. In-line particulate detector assembly 100 may also be directly positioned within a sidewall of pipeline 50.

Figure 2:
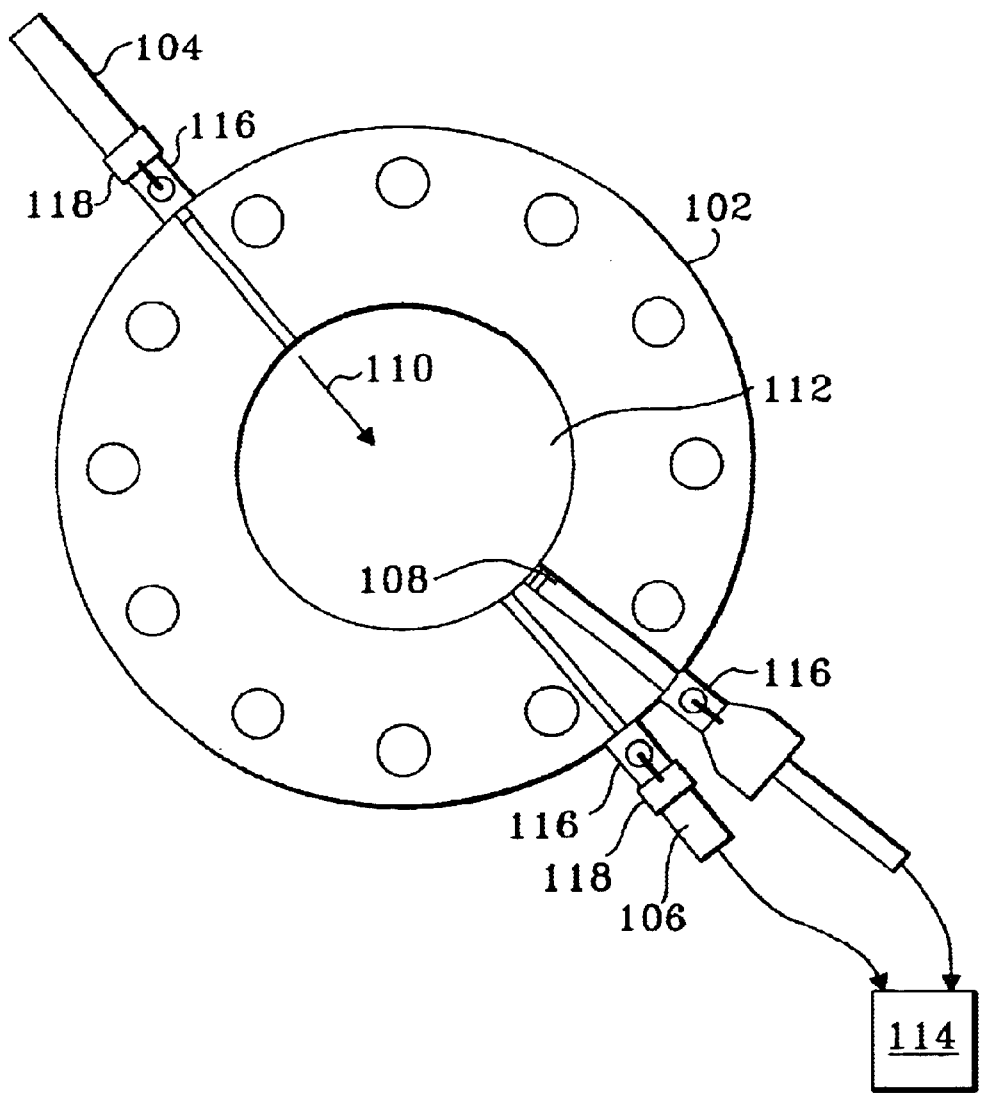
FIG. 2 is an enlarged schematic cross-sectional side elevation view of an in-line particulate detector in accordance with one embodiment of the instant invention.

In-line particulate detector assembly 100 comprises housing 102, a light source 104, a first photodetector 106 and a second photodetector 108, as shown in FIG. 2.

Light source 104 Is positioned within housing 102 so as to enable light source 104 to emit a light beam 110 within an interior flow portion 112 of housing 102. First photodetector 106 is disposed opposite light source 104 so as to be optically coupled with light source 104. Typically, first photodetector 106 is disposed within housing 102 opposite and substantially normal to light source 104 such that most of the full strength of a generated light beam 110 is detected by first photodetector 106 when little or no particles or other interfering substances are located within interior flow portion 112 of housing 102.

Second photodetector 108 is positioned within housing 102 adjacent to first photodetector 106. Second photodetector 108 is angularly offset from the normal unimpeded path of light between light source 104 and first photodetector 106, typically in the range between about 10° to about 60°. A key feature of this invention is the placement of second photodetector 108 slightly offset from light source 104. This offset position maximizes the collection of scattered light while retaining the simplicity of a single photodetector for scattered light detection.

When little or no particles or other interfering substances are present within a fuel flow 60 traveling through interior flow portion 112 of housing 102, second photodetector 108 will sense a baseline level of light reflected from first photodetector 106 and Rayleigh scattering from gas molecules within fuel flow 60 (FIG. 1).

When particles or other interfering substances are present within fuel flow 60 flowing through interior flow portion 112 (FIG. 2) of housing 102, light beam 110 will be scattered by these particles and the light intensity reaching second photodetector 108 will increase above the baseline level and light intensity reaching first photodetector 106 will decrease. The ratio of light intensities indicated by first and second photodetectors 106, 108 provides a sensitive measure of the presence of particles and the amount of particles in fuel flow 60.

Typically, fuel flow 60 comprises a natural gas, for example, methane, or propane, hexane, heptane, gas derived from coal, or the like. As discussed above, fuel flow 60 flows from fuel source 56 to fuel consumer 10 through pipeline 50 and interior flow portion 112 of housing 102.

Circuitry 114 is coupled to first and second photodetectors 106, 108 to measure the presence and quantity of particles when exposed to a fuel flow 60 between inlet 52 and outlet 54.

In one embodiment, circuitry 114 includes a power input, an amplifier and a processor for monitoring the signals from first and second photodetectors 106, 108 and generating an output signal. In another embodiment, circuitry 114 further comprises an amplifier and a computer for processing signals and generating a particulate level report or display.

A control structure is inputted into circuitry 116, for example, by programming into memory of an application specific integrated circuit (ASIC) or is embedded in the form of algorithms in one or more computers 119 such as a work station. Other types of computers can be used, however, such as a minicomputer, a microcomputer, or a supercomputer, for example. The programming or algorithm performed may be programmed in C, C++, JAVA, Basic, MATLAB, FORTRAN, or other programming languages.

If the ratio of light intensities indicated by first photodetector 106 and second photodetectors 108 is above a setpoint, indicating contamination, circuitry 114 may initiate a system control. For example, limit fuel consumer 10, to low load operation. Additionally, if the ratio of light intensities rises above a setpoint, circuitry 114 may initiate an algorithm to look at combustion system anomalies, or, for example, sound an alarm or otherwise alert a system user.

While the Instant invention is shown connected to a pipeline 50 for a fuel consumer 10, this invention could also be applied to monitor the quality of process gases, not necessarily intended for combustion. Additionally, the instant invention can be utilized for monitoring gas quality at the exit of a cryogenic gas processing system; monitoring gas quality at the custody transfer point between a gas producer and a gas transmission company; monitoring gas quality at the custody transfer point between a gas transmission company and a local distribution company; monitoring gas quality at a compressor station used to compress gas for natural gas powered vehicles, or the like.

Light source 104 may comprise a laser diode light source or the like. The advantage of laser light over a collimated beam of non-laser light is the combination of low divergence angle with high intensity and relatively high electrical efficiency. Light can be collimated from a conventional light source by spacing two slits far apart, however, the intensity is low relative to the power generated by the source.

Photodetectors 106, 108 may comprise photodiodes or the like. The advantage of solid state photodiodes is that they are inexpensive, very compact, and durable. While photodiodes are not as sensitive as traditional photomultipler tubes, with proper amplification, the sensitivity of photodiodes is sufficient to sense low levels of particles.

In one embodiment, a light trap is disposed adjacent first photodetector 106 to minimize the light reflected therefrom.

In one embodiment, ball valves 116 and sight glasses 118 are disposed between light source 104 and interior flow portion 112 and between each photodetector 106, 108 and interior flow portion 112 to make in-line particulate detector assembly 100 serviceable in the field without interruption of fuel flow 60.

In one embodiment, second photodetector 108 is positioned in close proximity to internal flow portion 112 of housing 102 to maximize the intensity of scattered light reaching second photodetector 108.

Figure 3:
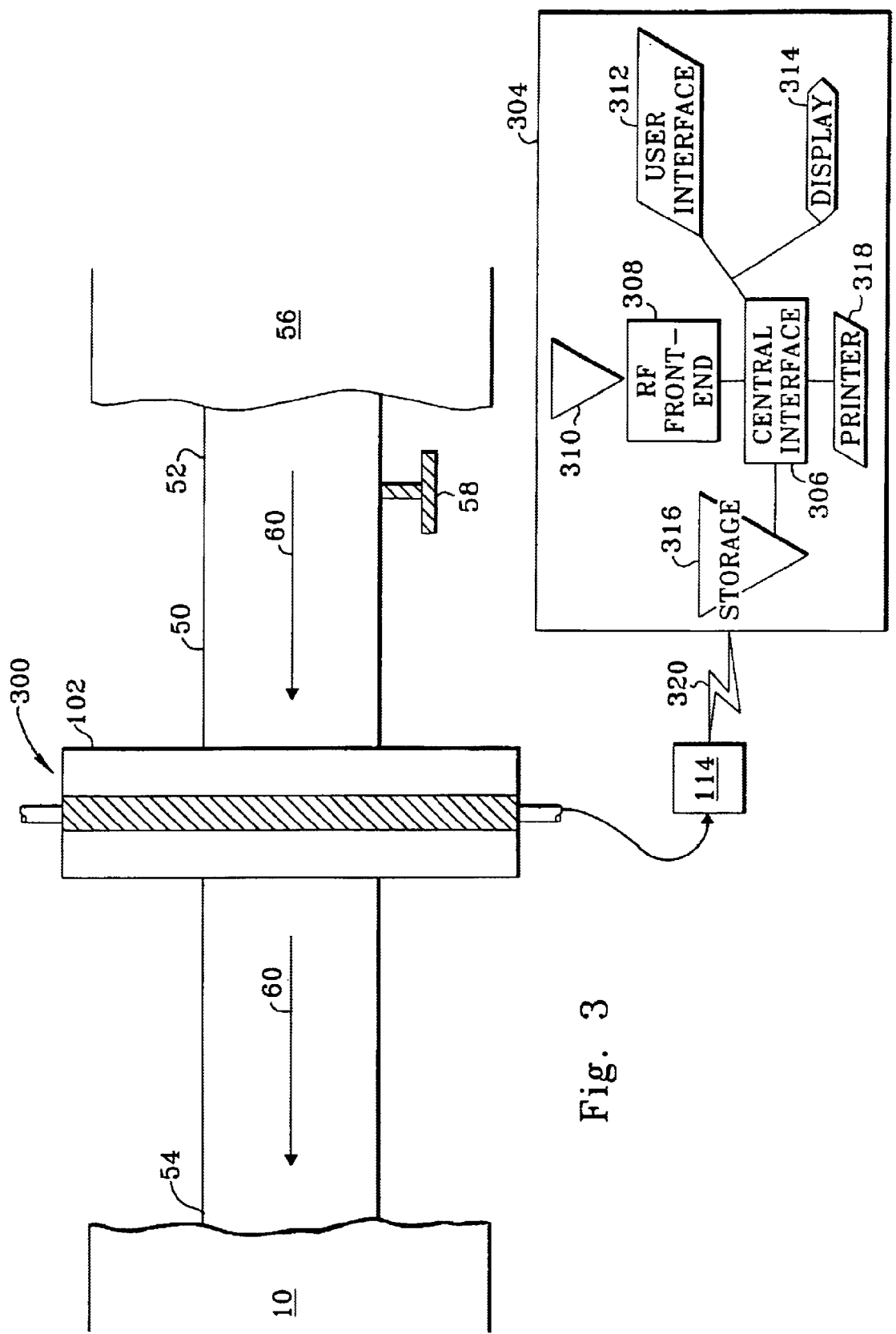
FIG. 3 is a schematic, cross-sectional side elevation view of a pipeline and a remote in-line particulate detector in accordance with one embodiment of the instant invention.

A remote in-line particulate detector assembly 200 is shown in FIG. 3. This embodiment is similar in all respects to the in-line particulate detector assembly in FIGS. 1 and 2, except that circuitry 114 comprises a remote unit for transmitting signals from assembly 200.

A remote station 304 provides a communication base for interaction with a respective remote unit. Remote station 304 typically comprises a central interface 306, a radio frequency (RF) front-end 308, an antenna, and user interface related peripheral devices including a user interface 312, a display 314, data storage 316 and a printer 318 for enabling a user to input or extract relevant information into central interface 306. Peripheral devices as defined in this application include any device for storing particulate measurement or analysis information and intelligibly communicating the same to a system user, and include such devices as printers, hard disk drives, floppy disk drives, cathode ray tubes (CRTs) and keyboards. While only one set of respective peripheral devices is shown for a respective central interface 306, any number of peripheral drives may be utilized and are within the scope of the instant invention.

Methods for determining gas quality using remote in-line particulate detector assembly 200 are previously discussed.

Communication between remote station 304 and a respective remote unit is by way of a communications system 320, such as a "goo-synchronous" "L-band" satellite system, a "Little Leo" satellite system, a two-way paging system, a modem connection or any communication system capable of two-way communication between remote station 304 and a respective remote unit.

While only certain features of the invention have been illustrated and described, many modifications and changes will occur to those skilled in the art. It is, therefore, to be understood that the appended claims are intended to cover all such modifications and changes as fall within the true spirit of the invention.

What is claimed is:

1. An in-line particulate detector comprising:
   a housing having an inner flow portion in flow communication with a fluid inlet and a fluid outlet, which housing is installed in-line between adjacent portions of a pipeline in a system and is removably disposable between the adjacent portions of the pipeline to permit a fuel flow from a fuel source through said inner flow portion to a fuel consumer;

a laser diode light source disposed within said housing for emitting a light beam within said inner flow portion;

a first photodiode disposed within said housing positioned opposite and substantially normal to said laser diode light source such that substantially full strength of an unimpeded generated light beam is detected by said first photodiode;

a second photodiode disposed within said housing adjacent said first photodiode and offset from a normal unimpeded path between said laser diode and said first photodiode such that a baseline level of an unimpeded generated light beam is detected by said second photodiode;

circuitry coupled to said first and second photodiodes to monitor the ratio of light intensities measured by said first and second photodiode to indicate the presence of particulate within an introduced fuel flow; and a control structure inputted into said circuitry to initiate a system control based on the ratio of light intensities.

2. An in-line particulate detector in accordance with claim 1, wherein said flow is natural gas.

3. An in-line particulate detector in accordance with claim 1, wherein said flow is selected from the group consisting of propane, hexane, heptane, gas derived from coal, and methane.

4. An in-line particulate detector in accordance with claim 1, wherein a fuel containing particulates will cause a generated light beam to be scattered, and the light intensity measured by second photodiode will increase above the baseline level and the light intensity reaching first photodiode will decrease.

5. An in-line particulate detector in accordance with claim 1, wherein said control structure is inputted into said circuitry by programming into memory of an application specific integrated circuit.

6. An in-line particulate detector in accordance with claim 1, wherein said control structure is inputted into said circuitry by being embedded in the form of algorithms in one or more computers.

7. An in-line particulate detector in accordance with claim 6, wherein said computer is selected from the group consisting of a workstation, a minicomputer, a microcomputer, and a supercomputer.

8. An in-line particulate detector in accordance with claim 1, wherein said control structure is programmed in a language selected from the group of C, C++, Basic, MATLAB, and FORTRAN.

9. An in-line particulate detector comprising;

a housing having an inner flow portion in flow communication with a fluid inlet and a fluid outlets, which housing is installed in-line between adjacent portions of a pipeline in a system and is removably disposable between the adjacent portions of the pipeline to permit a fuel flow from a fuel source through said inner flow portion to a fuel consumer;

a laser diode light source disposed within said housing for emitting a light beam within said inner flow portion;

a first photodiode disposed within said housing positioned opposite and substantially normal to said diode light source such that substantially full strength of an unimpeded ed generated light beam is detected by said first photodiode;

a second photodiode disposed within said housing adjacent said first photodiode and offset from a normal unimpeded path between said laser diode and said first photodiode such that a baseline level of an unimpeded generated light beam is detected by said second photodiode;

circuitry coupled to said first and second photodiode to monitor the ratio of light intensities measured by said first and second photodiodes to indicate the presence of particulate within an introduced fuel flow;

a control structure inputted into said circuitry to initiate a system control based on the ratio of light intensities; and at least one remote unit for transmitting signals generated from said first and second photodiodes;

a central station; and a communications link.

10. A remote in-line particulate detector in accordance with claim 9, wherein said signals represent light intensities measured by said first and second photodetectors.

11. A remote in-line particulate detector in accordance with claim 9, wherein said remote system comprises a central interface coupled to said at least one remote unit, wherein said central interface is adapted to control communications between said central station and said at least one remote unit.

12. A remote in-line particulate detector in accordance with claim 9, wherein said communications link comprises a radio frequency (RF) front end.

13. A remote in-line particulate detector in accordance with claim 9 wherein said communication link comprises a satellite.

14. A remote in-line particulate detector in accordance with claim 9, wherein said communication link comprises a link.

15. A remote incline particulate detector in accordance with claim 9 wherein said remote system further comprises an antenna.

16. A remote in-line particulate detector in accordance with claim 9 wherein said remote system further comprises at least one user interface device.

17. An in-line particulate detector comprising:

a housing having an inner flow portion in flow communication with a fluid inlet and a fluid outlet, which housing is installed in-line between adjacent portions of a pipeline in a system and is removably disposable between the adjacent portions of the pipeline to permit a fuel flow from a fuel source through said inner flow portion to a fuel consumer;

a means for emitting a light beam within said inner flow portion;

a first means for detecting substantially full strength of an unimpeded light beam generated by said means for emitting;

a second means offset from a normal unimpeded path between said light emitting means and said first means for detecting a baseline level of unimpeded light beam generated by said means for emitting;

a means for comparing the light intensities detected by said first and second means for detecting, to determine the presence of particulate within an introduced flow; and a control means for receiving from said comparing means a signal to initiate a system control based on the ratio of light intensities.

18. An in-line particulate detector in accordance with claim 17, wherein said flow is natural gas.

19. An in-line particulate detector in accordance with claim 17, wherein said now is selected from the group consisting of propane, hexane, heptane, gas derived from coal, and methane.

20. An in-line particulate detector in accordance with claim 17, wherein a fuel containing particulates will cause a generated light beam to be scattered, find the light intensity measured by said second means for detecting will increase above the baseline level and the light intensity reaching said first means for detecting will decrease.

21. An in-line particulate detector in accordance with claim 17, wherein a control structure is inputted into said circuitry.

22. An in-line particulate detector in accordance with claim 21, wherein said control structure is inputted into said circuitry by programming into memory of an application specific integrated circuit.

23. An in-line particulate detector in accordance with claim 21, wherein said control structure is inputted into said circuitry by being embedded in the form of algorithms in one or more computers.

24. An in-line particulate detector in accordance with claim 23, wherein said computer is selected from the group consisting of a workstation, a minicomputer, a microcomputer, and a supercomputer.

25. An in-line particulate detector in accordance with claim 21, wherein said control structure is programmed in a language selected from the group of C, C++, Basic, MATLAB, and FORTRAN.

26. An in-line particulate detector comprising:

a housing having an inner flow portion in flow communication with a fluid inlet and a fluid outlet; which housing is installed in-line between adjacent portions of a pipeline in a system and is removably disposable between the adjacent portions of the pipeline to permit a fuel flow from a fuel source through said inner flow portion to a fuel consumer;

a laser diode light source disposed within said housing for emitting a light beam within said inner flow portion;

a first photodiode disposed within said housing positioned opposite and substantially normal to said laser diode light source such that substantially full strength of an unimpeded generated light beam is detected by said first photodiode;

a second photodiode disposed within said housing adjacent said first photodiode and offset from a normal unimpeded path between said laser diode and said first photodiode such that a baseline level of an unimpeded generated light beam is detected by said second photodiode;

circuitry coupled to said first and second photodiode to monitor the ratio of light intensities measured by said first and second photodiodes to indicate the presence of particulate within an introduced flow; and a control structure inputted into said circuitry to initiate a system control based on the ratio of light intensities.

27. An in-line particulate detector for insertion within a pipeline, said detector comprising:

a laser diode light source to be disposed within said pipeline for emitting a light beam within an inner flow portion of said pipeline, the inner flow portion in flow communication with a fluid inlet and a fluid outlet;

a first photodiode to be disposed within said pipeline positioned opposite and substantially normal to said laser diode light source such that substantially full strength of an unimpeded generated light beam is detected by said first photodiode;

a second photodiode to be disposed within said pipeline adjacent said first photodiode and offset from a normal unimpeded path between said laser diode and said first photodiode such that a baseline level of unimpeded generated light beam is detected by said second photodiode;

circuitry coupled to said first and second photodiode to monitor the ratio of light intensities measured by said first and second photodiodes to indicate the presence of particulate within an introduced flow; and a control structure inputted into said circuitry to initiate a system control based on the ratio of light intensities.

\* \* \* \* \*

UNITED STATES PATENT AND TRADEMARK OFFICE
CERTIFICATE OF CORRECTION

PATENT NO. : 6,710,878 B1 Page 1 of 1
DATED : March 23, 2004
INVENTOR(S) : Dean

It is certified that error appears in the above-identified patent and that said Letters Patent is hereby corrected as shown below:

Column 5,
Line 49, delete "outlets" and insert -- outlet --.

Signed and Sealed this

Twenty-eighth Day of March, 2006

JON W. DUDAS
*Director of the United States Patent and Trademark Office*